United States Patent
Yoshida et al.

(10) Patent No.: US 8,357,539 B2
(45) Date of Patent: Jan. 22, 2013

(54) ACTIVATED PARTIAL THROMBOPLASTIN TIME MEASURING REAGENT, ACTIVATED PARTIAL THROMBOPLASTIN TIME MEASURING METHOD, AND DETERMINATION METHOD FOR DETERMINING PRESENCE OR ABSENCE OF BLOOD COAGULATION INHIBITOR

(75) Inventors: Kazuyo Yoshida, Kobe (JP); Masahiro Okuda, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 12/976,681

(22) Filed: Dec. 22, 2010

(65) Prior Publication Data

US 2011/0159597 A1 Jun. 30, 2011

(30) Foreign Application Priority Data

Dec. 25, 2009 (JP) .................. 2009-294107

(51) Int. Cl.
*G01N 33/86* (2006.01)
*G01N 33/48* (2006.01)

(52) U.S. Cl. .................. 436/69; 436/8; 436/18; 436/63; 436/71; 436/79; 252/408.01; 435/13; 73/64.41; 600/369

(58) Field of Classification Search ............... 436/8, 16, 436/18, 63, 69, 71, 79, 174; 252/408.1; 435/13; 73/64.41; 600/369; 564/295

See application file for complete search history.

(56) References Cited

U.S. PATENT DOCUMENTS

| 5,151,192 | A | * | 9/1992 | Matkovich et al. | ........... 210/646 |
| 5,262,325 | A |   | 11/1993 | Zimmermann et al. | |
| 5,338,677 | A |   | 8/1994 | Zimmermann et al. | |
| 5,506,146 | A | * | 4/1996 | Josef | ............... 436/69 |
| 6,090,570 | A | * | 7/2000 | Kraus | ............. 435/13 |
| 6,100,072 | A | * | 8/2000 | Brucato et al. | .............. 435/69.7 |
| 2003/0143759 | A1 | * | 7/2003 | Dahlback | ...................... 436/538 |
| 2004/0091952 | A1 | * | 5/2004 | Okuda | ............ 435/13 |

FOREIGN PATENT DOCUMENTS

| CA | 2096212 A1 | 11/1993 |
| EP | 0570356 A1 | 11/1993 |
| WO | 92/17203 A1 | 10/1992 |

OTHER PUBLICATIONS

Jacobsen et al. Thrombosis Journal, vol. 4:3, Jan. 25, 2006, pp. 1-7.*
Kazuhiko Kagawa, "Blood Coagulation Correction Test," Kensa to gijutu, Aug. 2006, pp. 735-741, vol. 34, No. 8.
Extended European Search Report issued Mar. 3, 2011 in European Patent Application No. 10196681.0 to Sysmex Corporation.

* cited by examiner

Primary Examiner — Maureen Wallenhorst
(74) Attorney, Agent, or Firm — Sughrue Mion, PLLC

(57) ABSTRACT

An activated partial thromboplastin time measuring reagent, including a first reagent containing a phospholipid and an activator and a second reagent containing a herparin neutralizer and a calcium salt is disclosed. An activated partial thromboplastin time measuring method, and a determination method for determining a presence or absence of a blood coagulation inhibitor are also disclosed.

16 Claims, 2 Drawing Sheets

ACTIVATED PARTIAL THROMBOPLASTIN TIME MEASURING REAGENT, ACTIVATED PARTIAL THROMBOPLASTIN TIME MEASURING METHOD, AND DETERMINATION METHOD FOR DETERMINING PRESENCE OR ABSENCE OF BLOOD COAGULATION INHIBITOR

FIELD OF THE INVENTION

The present invention relates to an activated partial thromboplastin time measuring reagent, an activated partial thromboplastin time measuring method, and a determination method for determining a presence or absence of a blood coagulation inhibitor.

BACKGROUND

Among patients who are the subjects of blood coagulation tests, there are patients who are treated with heparin as a therapeutic drug for thrombi. Meanwhile, there are patients for whom a catheter connected to a heparin lock which is filled with saline containing heparin is used, in order to prevent blood coagulation reactions from occurring in the catheter when drip infusion is performed. Test plasma collected from these patients may contain extrinsic heparin. Use of such test plasma for measuring an activated partial thromboplastin time (APTT) results in a prolonged blood coagulation time due to the influence of the heparin.

U.S. Pat. No. 5,262,325 discloses a method for removing the influence of extrinsic heparin contained in test plasma on an APTT measurement. In the method, the test plasma is neutralized by a heparin neutralizer and then an APTT is measured, thereby removing the influence of heparin contained in the test plasma. However, according to the method disclosed in U.S. Pat. No. 5,262,325, it is necessary to add in advance a heparin neutralizer in the test plasma. Therefore, the steps of the APTT measurement have been burdensome. Moreover, according to the method disclosed in U.S. Pat. No. 5,262,325, it is necessary to always consider possible presence of heparin in the test plasma, when performing an APTT measurement. In particular, in medical sites, when performing an emergency APTT measurement, an APTT measurement may be performed without checking the presence or absence in the test plasma of extrinsic heparin.

Moreover, in recent years, also in a cross mixing test which uses an APTT measuring reagent, the influence of extrinsic heparin contained in test plasma has been a problem (Kensa to gijutu, vol. 34, no. 8, August, 2006, pp. 738-739). A cross mixing test is a test that detects coagulation factor deficiency in a patient and the presence of a blood coagulation inhibitor in test plasma, by measuring the blood coagulation time of mixed plasma obtained by mixing the test plasma and normal plasma. As described above, when extrinsic heparin is contained in test plasma, the blood coagulation time is prolonged. Therefore, also in a cross mixing test, if extrinsic heparin is contained in the test plasma, the presence of a blood coagulation inhibitor that is an intrinsic factor may not be detected accurately.

SUMMARY OF THE INVENTION

The scope of the present invention is defined solely by the appended claims, and is not affected to any degree by the statements within this summary.

A first aspect of the present invention is an activated partial thromboplastin time measuring reagent, comprising a heparin neutralizer.

A second aspect of the present invention is a reagent used for measuring an activated partial thromboplastin time after a test plasma and a reagent containing a phospholipid and an activator have been mixed, the reagent comprising: a heparin neutralizer; and a calcium salt.

A third aspect of the present invention is an activated partial thromboplastin time measuring method comprising: a first mixing step of mixing a test plasma and a first reagent containing a phospholipid and an activator; a second mixing step of mixing a specimen obtained in the first mixing step and a second reagent containing a heparin neutralizer and a calcium salt; and a step of measuring a coagulation time of a specimen obtained in the second mixing step.

A forth aspect of the present invention is a determination method for determining a presence or absence of a blood coagulation inhibitor in a test plasma, the method comprising: a preparation step for preparing measurement specimens by mixing a normal plasma and a test plasma in which the blood coagulation inhibitor is suspected of being present, in at least three different ratios, a first mixing step of mixing each of the measurement specimens obtained in the preparation step and a first reagent containing a phospholipid and an activator; a second mixing step of mixing each of specimens obtained in the first mixing step and a second reagent containing a heparin neutralizer and a calcium salt; a step of measuring a coagulation time of each of specimens obtained in the second mixing step; and a step of determining the presence or absence of the blood coagulation inhibitor in the test plasma based on the coagulation time of each of the specimens obtained in the measuring step.

DETAILED DESCRIPTION OF THE PREFERRED EMBODIMENTS

Figure 1:
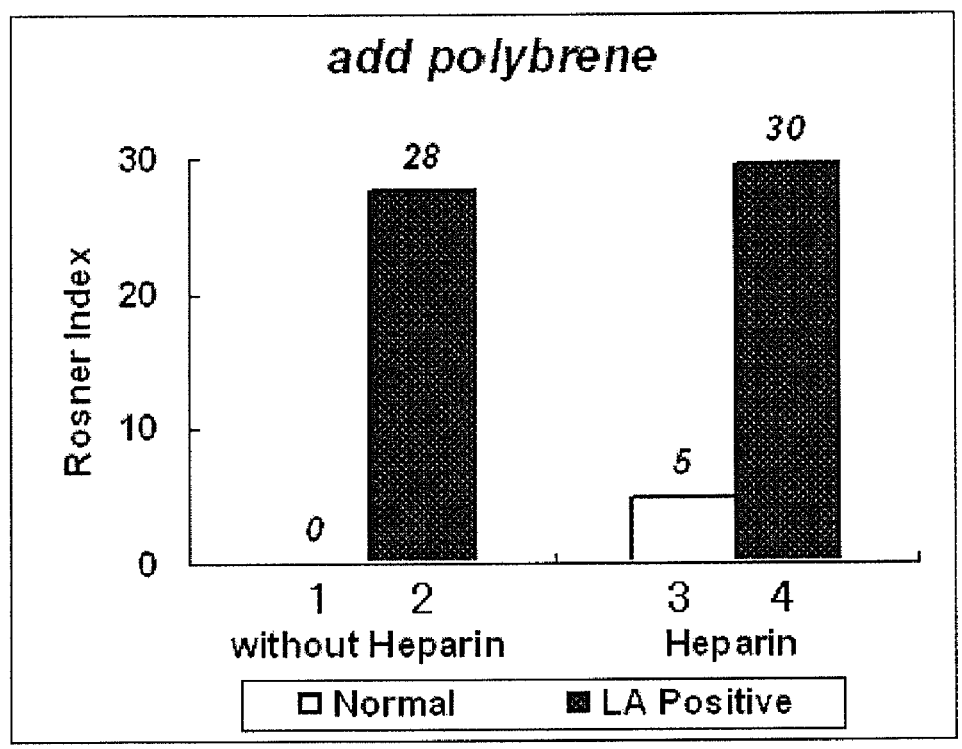
FIG. 1 shows a bar graph of Rosner index value calculated based on activated partial thromboplastin time (APTT) obtained from APTT measurement using a calcium solution containing polybrene.

An activated partial thromboplastin time (APTT) measuring reagent according to the present embodiment includes a heparin neutralizer. The APTT measuring reagent may have a configuration including, for example, a first reagent containing a phospholipid and an activator, and a second reagent containing a heparin neutralizer and a calcium salt. Alternatively, the APTT measuring reagent may have a configuration including, for example, a first reagent containing a phospholipid and an activator, a second reagent containing a calcium salt, and a third reagent containing a heparin neutralizer. Here, the third reagent may be added after the first reagent has been added and before the second reagent is added. Alternatively, the third reagent may be added after the first reagent and the second reagent have been added.

The present inventors have found that with respect to an APTT measuring reagent, when a heparin neutralizer is added into a reagent containing a calcium salt, an APTT measurement can be performed without causing precipitation and without being influenced by heparin contained in test plasma.

Accordingly, in the present embodiment, it is preferable that the APTT measuring reagent containing a heparin neutralizer has a configuration which includes a first reagent containing a phospholipid and an activator, and a second reagent containing a heparin neutralizer and a calcium salt.

The activated partial thromboplastin time (APTT) measuring reagent according to the present embodiment includes a first reagent containing a phospholipid and an activator, and a second reagent containing a heparin neutralizer and a calcium salt.

The phospholipid in the first reagent may be any phospholipid as long as it can be generally used in an APTT measuring reagent, and is not limited to a particular phospholipid. Examples of the phospholipid may include phosphatidylserine, phosphatidylethanolamine, phosphatidylcholine, and phosphatidylglycerol. Moreover, the phospholipid may be a natural phospholipid such as a phospholipid derived from bovine brain, rabbit brain, human placenta, soybean, or egg yolk, or a synthetic phospholipid. Preferably, the phospholipid is a cephalin derived from rabbit brain, a cephalin derived from soybean, a synthetic phospholipid, or the like.

The concentration of the phospholipid in the first reagent may be set as appropriate in accordance with the type of phospholipid, the APTT measurement condition, and the like, and is not limited to a particular concentration. An example of the concentration of the phospholipid in the first reagent may be 20 to 200 μg/mL, and preferably 50 to 150 μg/mL. When a cephalin derived from rabbit brain, a cephalin derived from soybean, or a synthetic phospholipid is used as the phospholipid, the concentration of the phospholipid in the first reagent is preferably 20 to 200 μg/mL, and more preferably, 50 to 150 μg/mL.

The activator in the first reagent may be any substance as long as it activates contact factors, and is not limited to a particular activator. For example, at least one selected from the group consisting of ellagic acid, kaolin, celite, colloidal silica, silicic anhydride, and the like may be used. Preferable activators for the present embodiment are ellagic acid, and colloidal silica.

The concentration of the activator in the first reagent may be set as appropriate in accordance with the type of activator, the APTT measurement condition, and the like, and is not limited to a particular concentration. For example, the concentration of the activator in the first reagent may be 5 to 1000 μg/mL, and preferably 20 to 500 μg/mL. When ellagic acid is used as the activator, the concentration of the activator in the first reagent is preferably 5 to 100 μg/mL, and more preferably 20 to 50 μg/mL.

Further, in addition to the phospholipid and the activator, the first reagent may further include other components that can be added to the APTT measuring reagent. In this case, examples of other components may be a buffer, a preservative, an antioxidant, and the like.

Here, the buffer may be any buffer as long as it is a publicly-known buffer used in an APTT measuring reagent, and is not limited to a particular buffer. Examples of the buffer are HEPES, TRIS, MOPS, and the like. Preferably, the pH of the first reagent is 5 to 9, and more preferably, 6 to 8. The pH of the first reagent may be adjusted by using the buffer.

The preservative may be any preservative as long as it is a publicly-known preservative used in an APTT measuring reagent, and is not limited to a particular preservative. Examples of the preservative include sodium azide, phenol, an antibiotic (ciprofloxacin), and the like, and preferably, the preservative is phenol. The concentration of the preservative in the first reagent may be adjusted as appropriate, and is 1 to 5 mg/mL, for example.

The antioxidant may be any antioxidant as long as it is a publicly-known antioxidant used in an APTT measuring reagent, and is not limited to a particular antioxidant. Examples of the antioxidant include butylhydroxyanisol, and the like.

The heparin neutralizer in the second reagent according to the present embodiment may be any heparin neutralizer as long as it is a publicly-known heparin neutralizer that does not influence an APTT measurement, and is not limited to a particular heparin neutralizer. For example, at least one selected from the group consisting of polybrene, protamine sulfate, heparinase, and the like may be used as the heparin neutralizer. Preferably, the heparin neutralizer according to the present embodiment is polybrene.

The concentration of the heparin neutralizer in the second reagent may be set as appropriate in accordance with the type of heparin neutralizer, the APTT measurement condition, and the like, and is not limited to a particular concentration. Examples of the concentration of the heparin neutralizer in the second reagent include 0.5 to 100 μg/mL. When polybrene is used as the heparin neutralizer, the concentration of the polybrene in the second reagent is preferably 5 to 50 μg/mL, and more preferably 10 to 20 μg/mL.

The calcium salt in the second reagent may be any calcium salt as long as it can be generally used in an APTT measuring reagent, and is not limited to a particular calcium salt. For example, either a salt of an inorganic acid and calcium, or a salt of an organic acid and calcium may be used. Examples of a salt of an inorganic acid and calcium include calcium chloride, calcium nitrite, calcium sulfate, calcium carbonate, and the like. Examples of a salt of an organic acid and calcium include calcium lactate, calcium tartrate, and the like. The calcium salt in the second reagent is preferably a salt of an inorganic acid and calcium, and more preferably, calcium chloride.

The concentration of the calcium salt in the second reagent may be set as appropriate in accordance with the type of calcium salt, the APTT measurement condition, and the like, and is not limited to a particular concentration. Examples of the concentration of the calcium salt in the second reagent include 15 to 50 mM, and preferably, the concentration of the calcium salt in the second reagent is 20 to 30 mM. When calcium chloride is used as the calcium salt, the concentration of the calcium salt in the second reagent is preferably 15 to 30 mM, and more preferably, 20 to 25 mM.

In addition to the heparin neutralizer and the calcium salt, the second reagent may further include other components that can be added to the APTT measuring reagent. Examples of other components include a buffer, a preservative, and the like.

Here, as the buffer, a buffer similar to that of the first reagent may be used. The pH of the second reagent is preferably 5 to 9, and more preferably, 6 to 8. The pH of the second reagent may also be adjusted by using the above described buffer in the same manner as the first reagent.

As the preservative, a preservative similar to that of the first reagent may be used. The concentration of the preservative in the second reagent may be adjusted as appropriate, and is 1 to 5 mg/mL, for example.

The reagent according to the present embodiment, which is used for measuring an activated partial thromboplastin time after a test plasma and a reagent containing a phospholipid and an activator are mixed, and which contains a heparin neutralizer and a calcium salt, is the same as the second reagent of the APTT measuring reagent of the present embodiment described above.

An activated partial thromboplastin time (APTT) measuring method according to the present embodiment is performed by using the APTT measuring reagent of the present embodiment described above. To be specific, the APTT measuring method according to the present embodiment includes a first mixing step of mixing a test plasma and the first reagent containing a phospholipid and an activator, a second mixing step of mixing a specimen obtained in the first mixing step and the second reagent containing a heparin neutralizer and a calcium salt, and a step of measuring a coagulation time of the specimen obtained in the second mixing step.

The first mixing step may be any method of mixing the test plasma and the first reagent containing a phospholipid and an activator, and the order of addition of the test plasma and the first reagent is not limited to a particular order.

Here, the test plasma may be any portion that is obtained by removing blood cells from the whole blood of the patient, and is not limited to a particular plasma. The method for obtaining test plasma is publicly known. Examples of the method for obtaining test plasma include a method in which an anticoagulant is added to the blood obtained from the patient, the mixture is centrifuged, and the supernatant of the centrifuged mixture is removed, to yield the test plasma. Further, alternatively to the test plasma obtained in the above method, commercially available plasma may be used. Examples of the commercially available plasma include normal plasma, blood coagulation factor deficient plasma, plasma containing a blood coagulation inhibitor, and the like. Examples of the normal plasma include COAGUTROL N (provided by Sysmex Corp.), standard human plasma for blood coagulation test (provided by Sysmex Corp.), and the like. Examples of the blood coagulation factor deficient plasma include factor-VIII deficient plasma (provided by Sysmex Corp.), factor-IX deficient plasma (provided by Sysmex Corp.), and the like. Examples of the plasma containing a blood coagulation inhibitor include LA positive plasma (provided by George King Bio-Medical, Inc.), FACTOR VIII DEFICIENT PLASMA WITH INHIBITOR (provided by George King Bio-Medical, Inc.), and the like. Further, the test plasma may be diluted as appropriate in accordance with the APTT measurement condition, and the like.

It should be noted that the first reagent used in the first mixing step is a reagent similar to the first reagent in the APTT measuring reagent of the present embodiment described above.

The reaction temperature in the first mixing step may be set as appropriate in accordance with the mixing ratio of the test plasma to the first reagent, the dilution rate of the test plasma, and the like, and is not limited to a particular temperature. For example, the reaction temperature may be 25° C. to 45° C., preferably 30° C. to 40° C., and more preferably 35° C. to 38° C.

The reaction time in the first mixing step may also be set as appropriate in accordance with the mixing ratio of the test plasma to the first reagent, the dilution rate of the test plasma, and the like, and is not limited to a particular time period. For example, the reaction time in the first mixing step may be 1 to 15 minutes, preferably 2 to 10 minutes, and more preferably 3 to 5 minutes.

The mixing ratio of the test plasma to the first reagent in the first mixing step may be set as appropriate in accordance with the dilution rate of the test plasma, the composition of the first reagent, and the like, and is not limited to a particular ratio. For example, the mixing ratio of the test plasma to the first reagent may be 8:2 to 2:8, and preferably 6:4 to 4:6, and more preferably 5:5, in volume.

The second mixing step may be any method of mixing the specimen obtained in the first mixing step and the second reagent containing a heparin neutralizer and a calcium salt, and the order of addition of the specimen obtained in the first mixing step and the second reagent is not limited to a particular order.

The second reagent used in the second mixing step is a reagent similar to the second reagent of the APTT measuring reagent of the present embodiment described above.

The reaction temperature in the second mixing step may be set as appropriate in accordance with the mixing ratio of the specimen obtained in the first mixing step to the second reagent, the dilution rate of the test plasma, and the like, and is not limited to a particular temperature. For example, the reaction temperature in the second mixing step may be 20° C. to 45° C., preferably 30° C. to 40° C., and more preferably 35° C. to 38° C.

The mixing ratio of the specimen obtained in the first mixing step and the second reagent in the second mixing step may be set as appropriate in accordance with the mixing ratio of the test plasma to the first reagent, the composition of the second reagent, and the like, and is not limited to a particular ratio. For example, the mixing ratio of the specimen obtained in the first mixing step to the second reagent is 8:2 to 5:5, preferably 7:3 to 6:4, and more preferably 2:1 in volume.

The measuring step may measure a coagulation time of the specimen obtained in the second mixing step, by using a publicly-known coagulation time measuring method generally used in an APTT measurement. Here, examples of the measuring method for measuring a coagulation time of a specimen include a method in which a person conducts, by using a stopwatch or the like, a visual measurement of the amount of time until coagulation of a specimen is confirmed, a method in which a coagulation time of a specimen is measured by means of an apparatus which measures optical information, and the like. A commercially available blood coagulation measuring apparatus for measuring a coagulation time of a specimen may also be used. Examples of the commercially available blood coagulation measuring apparatus include CS-2000i, CS-2100i (both provided by Sysmex Corp.), and the like.

A determination method for determining the presence or absence of a blood coagulation inhibitor in the test plasma, according to the present embodiment, is performed through a cross mixing test using the described above APTT measuring method according to the present embodiment. To be specific, the determination method according to the present embodiment includes: a preparation step for preparing measurement specimens by mixing a normal plasma and a test plasma in which a blood coagulation inhibitor is suspected of being present, in at least three different ratios; a first mixing step for mixing each of the measurement specimens obtained in the preparation step and the first reagent containing a phospholipid and an activator; a second mixing step for mixing each of the specimens obtained in the first mixing step and the second reagent containing a heparin neutralizer and a calcium salt; a step of measuring a coagulation time of each of the specimens obtained in the second mixing step; and a step of determining the presence or absence of a blood coagulation inhibitor in the test plasma, based on the coagulation time of each of the specimens obtained in the measuring step.

The preparation step may be any method of preparing measurement specimens used in a general cross mixing test. To be specific, the preparation step is a step of preparing measurement specimens by mixing a normal plasma and a test plasma in which a blood coagulation inhibitor is suspected of being present, in at least three different ratios. The order of addition of the normal plasma and the test plasma in which a blood coagulation inhibitor is suspected of being present is not limited to a particular order.

Here, the blood coagulation inhibitor may be any blood coagulation inhibitor other than heparin, contained in the test plasma. More specific examples of the blood coagulation inhibitor include lupus anticoagulant (LA), an acquired hemophilia factor, a coagulation factor inhibitor, and C1 inactivator, and the like.

It should be noted that the test plasma is a test plasma similar to that used in the APTT measuring method according to the present embodiment described above.

The normal plasma may be any portion that is obtained by removing blood cells from the whole blood of a healthy person, and is not limited to a particular plasma. The method for obtaining normal plasma is publicly-known. Examples of the method for obtaining normal plasma include a method in which an anticoagulant is added to the blood obtained from a healthy person and then the mixture is centrifuged, and the supernatant of the centrifuged mixture is removed, to yield the normal plasma. Further, alternatively to the normal plasma obtained in the above method, commercially available normal plasma may be used. Examples of the commercially available normal plasma include COAGUTROL N (provided by Sysmex Corp.), standard human plasma for blood coagulation test (provided by Sysmex Corp.), and the like. Further, the normal plasma may be diluted as appropriate in accordance with the APTT measurement condition, and the like.

The number of measurement specimens which each have a different mixing ratio of the test plasma to the normal plasma and are prepared in the preparation step may be any number which is greater than or equal to three. However, by increasing the number of measurement specimens, the accuracy of the determination method according to the present embodiment can be improved. An exemplary number of measurement specimens according to the present embodiment may be three to six.

The mixing ratio of the test plasma to the normal plasma in a measurement specimen prepared in the preparation step may be any mixing ratio, of test plasma to normal plasma, which is used for a measurement specimen in a general cross mixing test. To be specific, the mixing ratio of test plasma: normal plasma may be 0:10 to 10:0 in volume. That is, the mixing of the test plasma and the normal plasma in the preparation step includes a case where either the test plasma or the normal plasma is not mixed. For example, in a case where the number of measurement specimens which are prepared in the preparation step and which each have a different mixing ratio of the test plasma and the normal plasma is three, the test plasma and the normal plasma can be mixed in three different ratios of 10:0, 1:1, and 0:10 in volume.

The reaction temperature in the preparation step may be set as appropriate in accordance with the type of blood coagulation inhibitor to be determined, the dilution rate of the test plasma, the dilution rate of the normal plasma, and the like, and is not limited to a particular temperature. For example, the reaction temperature may be 25° C. to 45° C., preferably 30° C. to 40° C., and more preferably 35° C. to 38° C.

The reaction time in the preparation step may be set as appropriate in accordance with the type of blood coagulation inhibitor to be determined, the dilution rate of the test plasma, the dilution rate of the normal plasma, and the like. For example, in a case where the blood coagulation inhibitor which is a target of determination and is contained in the test plasma is a substance that instantaneously inhibits the blood coagulation reaction, such as lupus anticoagulant (LA), the reaction time in the preparation step may be 1 to 15 minutes, preferably 1 to 5 minutes, and more preferably 1 minute. In a case where the blood coagulation inhibitor which is a target of determination and is contained in the test plasma is a substance that relatively slowly inhibits the blood coagulation reaction, such as in the case of acquired hemophilia, the reaction time in the preparation step may be 0.2 hours to 5 hours, preferably 0.5 hours to 4 hours, and more preferably 1 hour to 3 hours.

In the first mixing step, the second mixing step, and the measuring step of the determination method for determining the presence or absence of a blood coagulation inhibitor in the test plasma, according to the present embodiment, processes similar to those performed in the first mixing step, the second mixing step, and the measuring step in the APTT measuring method according to the present embodiment are performed, respectively, on the measurement specimens prepared in the preparation step.

The determining step may be any publicly-known method for determining, in a cross mixing test, the presence or absence of a blood coagulation inhibitor contained in the test plasma, based on the coagulation time of each of the specimens obtained in the measuring step. Examples of the method include a determination method that uses the shape of the graph of the mixing ratio and coagulation time and a method that uses a Rosner index value. More specifically, in the case of the determination method which uses the shape of the graph of the mixing ratio and coagulation time, a graph is created having a horizontal axis of the mixing ratio of the test plasma and the normal plasma and a vertical axis of the coagulation time of specimens. If the graph has a concave shape, the presence of a blood coagulation inhibitor can be determined, and if the graph does not have a concave shape, the absence of a blood coagulation inhibitor can be determined. In the case of a determination method which uses a Rosner index value, a threshold value is set for the Rosner index value. If the Rosner index value calculated based on the coagulation time of a specimen is greater than or equal to the threshold value, the presence of a blood coagulation inhibitor can be determined. If the Rosner index value calculated based on the coagulation time of a specimen is less than the threshold value, the absence of a blood coagulation inhibitor can be determined.

A Rosner index value is a value calculated by the following formula (1):

Rosner index value=((APTT of specimen having mixing ratio of test plasma and normal plasma of 1:1)−(APTT of normal plasma))/(APTT of test plasma)×100     formula (1)

Hereinafter, the present invention will be described further in detail with reference to Examples. However, the present invention is not limited thereto.

EXAMPLE

Experimental Example 1

Addition of Polybrene to APTT Measuring Reagent (Reagent 1)

Reagent 1 was prepared by adding 3 μL of a 10 mg/mL polybrene solution (10 mg polybrene (provided by Nacalai Tesque, Inc.), 1 mL purified water) to 3 mL of a reagent containing a phospholipid and an activator of Thrombocheck APTT-SLA (provided by Sysmex Corp.).

(Reagent 2)

Reagent 2 was prepared by adding 3 μL of a 10 mg/mL polybrene solution to 3 mL of Actin FSL (provided by Sysmex Corp.).

(Reagent 3)

Reagent 3 was prepared by adding 3 μL of a 10 mg/mL polybrene solution to 3 mL of a reagent containing a phospholipid and an activator of HemosIL APTT-SP (provided by Mitsubishi Chemical Medience Corporation).

(Reagent 4)

Reagent 4 was prepared by adding 3 μL of a 10 mg/mL polybrene solution to 3 mL of a reagent containing a phospholipid and an activator of HemosIL SynthASil APTT (provided by Mitsubishi Chemical Medience Corporation).

(Reagent 5)

Reagent 5 was prepared by adding 3 μL of a 10 mg/mL polybrene solution to 3 mL of a 25 mM calcium solution (278 mg calcium chloride, 100 mL purified water).

Table 1 shows the type of phospholipid and activator of each Thrombocheck APTT-SLA, Actin FSL, HemosIL APTT-SP, and HemosIL SynthASil APTT.

TABLE 1

|  | Thrombocheck APTT-SLA | Actin FSL | HemosIL APTT-SP | HemosIL SynthASil APTT |
| --- | --- | --- | --- | --- |
| Phospholipid | synthetic phospholipid | rabbit brain derived cephalin and soybean derived cephalin | synthetic phospholipid | synthetic phospholipid |
| Activator | ellagic acid | ellagic acid | colloidal silica | light anhydrous silicic acid |

[Observation of Influence of the Addition of Polybrene to APTT Measuring Reagent]

The presence or absence of precipitation in each of reagents 1 to 5 was visually observed after 6 hours had elapsed. Table 2 shows the observation result.

TABLE 2

|  | Reagent 1 | Reagent 2 | Reagent 3 | Reagent 4 | Reagent 5 |
| --- | --- | --- | --- | --- | --- |
| Precipitation | + | + | + | + | − |

+: with precipitation
−: without precipitation

As is apparent from Table 2, each reagent containing a phospholipid and an activator for use in an APTT measurement caused precipitation by the addition of polybrene, irrespective of the type of phospholipid and the type of activator. On the other hand, it was apparent that a calcium solution for use in an APTT measurement did not cause precipitation in spite of the addition of polybrene.

Experimental Example 2

Preparation of Measurement Specimen (Measurement Specimen 1)

Measurement specimen 1 was prepared by heating COAGUTROL N (provided by Sysmex Corp.) at 37° C. for 1 minute.

(Measurement Specimen 2)

Measurement specimen 2 was prepared by heating lupus anticoagulant (LA) positive plasma (provided by George King Bio-Medical, Inc.) at 37° C. for 1 minute.

(Measurement Specimen 3)

COAGUTROL N was used as a normal plasma. As a test plasma, LA positive plasma (provided by George King Bio-Medical, Inc.) was used. Measurement specimen 3 was prepared by mixing the normal plasma and the test plasma at a ratio of 1:1, and then heating the mixture at 37° C. for 2 minutes.

(Measurement Specimen 4)

Measurement specimen 4 was prepared by adding Novo-Heparin (provided by Novo Nordisk A/S) to COAGUTROL N at a concentration of 0.5 U/mL, and heating the mixture at 37° C. for 2 minutes.

(Measurement Specimen 5)

COAGUTROL N was used as a normal plasma. As a test plasma, a mixture was used which had been obtained by adding Novo-Heparin (provided by Novo Nordisk A/S) to COAGUTROL N at a concentration of 0.5 U/mL. Then, measurement specimen 5 was prepared by mixing the normal plasma and the test plasma at a ratio of 1:1, and then heating the resultant mixture at 37° C. for 2 minutes.

(Measurement Specimen 6)

Measurement specimen 6 was prepared by adding Novo-Heparin (provided by Novo Nordisk A/S) to LA positive plasma (provided by George King Bio-Medical, Inc.) at a concentration of 0.5 U/mL, and heating the mixture at 37° C. for 2 minutes.

(Measurement Specimen 7)

COAGUTROL N was used as a normal plasma. As a test plasma, a mixture was used which had been obtained by adding Novo-Heparin to LA positive plasma (provided by George King Bio-Medical, Inc.) at a concentration of 0.5 U/mL. Then, measurement specimen 7 was prepared by mixing the normal plasma and the test plasma at a ratio of 1:1, and then heating the resultant mixture at 37° C. for 2 minutes.

[APTT Measurement]

An amount of 50 μL of measurement specimen 1 was dispensed into a cuvette. Then, 50 μL of the reagent containing the phospholipid and the activator of Thrombocheck APTT-SLA was added to the cuvette, and the mixture was heated at 37° C. for 3 minutes. Then, 50 μL of reagent 5, which was a calcium solution containing polybrene, was added to the cuvette, and the amount of time until coagulation of the specimen was detected was measured by a full automatic blood coagulation measuring apparatus CS-2000i (provided by Sysmex Corp.). Thus, a measurement value 1 was obtained.

The coagulation time of each of the measurement specimens 2 to 7 was measured using operations similar to those performed in the APTT measurement of measurement specimen 1, except that measurement specimen 2, measurement specimen 3, measurement specimen 4, measurement specimen 5, measurement specimen 6, or measurement specimen 7 was used, respectively, instead of measurement specimen 1. In this manner, measurement values 2 to 7 were obtained.

[Analysis of Cross Mixing Test Using Rosner Index Value]

FIG. 1 shows an analysis result of a cross mixing test using Rosner index values calculated by using the measurement values (APTT) of the coagulation times of the measurement specimens 1 to 7. Here, each Rosner index value was calculated by using the above formula (1). As the APTT of normal plasma in the formula (1), the measurement value 1 was used. A specific calculation formula is shown as a formula (2) below.

Rosner index value=((measurement value of mixed plasma)−(measurement value 1))/(measurement value of test plasma)×100      formula (2)

Bar graph 1 and bar graph 2 in FIG. 1 show Rosner index values which were obtained when a plasma not containing heparin was used. Here, bar graph 1 shows a Rosner index value which was obtained when the measurement value 1 was inserted as the "measurement value of test plasma" and the "measurement value of mixed plasma" in the formula (2). Bar graph 2 shows a Rosner index value which was obtained when the measurement value 2 was inserted as the "measurement value of test plasma" and the measurement value 3 was inserted as the "measurement value of mixed plasma" in the formula (2).

Bar graph 3 and bar graph 4 in FIG. 1 show Rosner index values which were obtained when a plasma containing heparin was used. Here, bar graph 3 shows a Rosner index value which was obtained when the measurement value 4 was inserted as the "measurement value of test plasma" and the measurement value 5 was inserted as the "measurement value of mixed plasma" in the formula (2). Bar graph 4 shows a Rosner index value which was obtained when the measurement value 6 was inserted as the "measurement value of test plasma" and the measurement value 7 was inserted as the "measurement value of mixed plasma" in the formula (2).

Experimental Example 3

Figure 2:
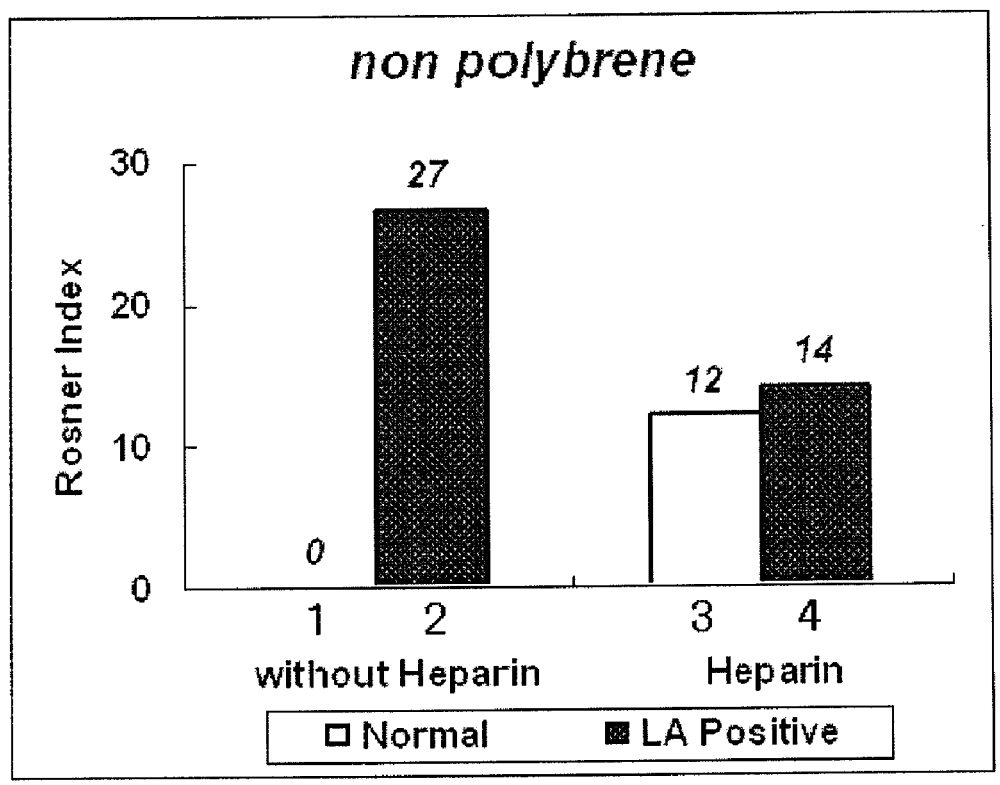
FIG. 2 shows a bar graph of Rosner index value calculated based on activated partial thromboplastin time (APTT) obtained from APTT measurement using a calcium solution not containing polybrene.

A cross mixing test using APTT measurements and Rosner index values was performed using operations similar to those in Experimental Example 2, except that a 25 mM calcium solution (278 mg calcium chloride, 100 mL purified water) not containing polybrene was used instead of reagent 5, which was a calcium solution containing polybrene used in Experimental Example 2. FIG. 2 shows an analysis result of the cross mixing test. With respect to bar graphs 1 to 4 in FIG. 2, as in the case of bar graphs 1 to 4 in FIG. 1, bar graph 1 and bar graph 2 show Rosner index values which were obtained when a plasma not containing heparin was used, and bar graph 3 and bar graph 4 show Rosner index values which were obtained when a plasma containing heparin was used.

With reference to bar graphs 1 and 2 in each of FIG. 1 and FIG. 2, it has been shown that an APTT measurement using a calcium solution containing polybrene can obtain Rosner index values similar to those obtained in an APTT measurement using a calcium solution not containing polybrene. Accordingly, it has been suggested that addition of polybrene to a calcium solution does not have an influence on an APTT measurement.

As apparent with reference to bar graph 3 and bar graph 4 in FIG. 2, in a case where an APTT measurement is performed on a plasma containing heparin of extrinsic origin by using a calcium solution not containing polybrene, there is substantially no difference between the Rosner index value of the normal plasma and the Rosner index value of the LA positive plasma. This makes a determination of LA positive or LA negative difficult. On the other hand, as apparent with reference to bar graph 3 and bar graph 4 in FIG. 1, in a case where a calcium solution containing polybrene is used, the influence of heparin of extrinsic origin is reduced. Accordingly, it is possible to make a determination of LA positive or LA negative, even when a plasma containing heparin of extrinsic origin is used.

From the results described above, it has been shown that use of a calcium solution containing polybrene does not have influence on the APTT measurement itself. Further, it has been shown that by using a calcium solution containing polybrene, an accurate APTT measurement can be performed even on a plasma containing heparin of extrinsic origin.

What is claimed is:

1. An activated partial thromboplastin time measuring reagent, comprising:
   a first reagent containing a phospholipid and an activator; and
   a second reagent containing a heparin neutralizer and a calcium salt.

2. The activated partial thromboplastin time measuring reagent according to claim 1, wherein
   the heparin neutralizer is polybrene.

3. The activated partial thromboplastin time measuring reagent according to claim 1, wherein
   the calcium salt is calcium chloride.

4. The activated partial thromboplastin time measuring reagent according to claim 1, wherein
   the activator is at least one selected from the group consisting of ellagic acid, colloidal silica, and silicic anhydride.

5. The activated partial thromboplastin time measuring reagent according to claim 1, wherein
   the phospholipid is at least one selected from the group consisting of phosphatidylserine, phosphatidylethanolamine, phosphatidylcholine, and phosphatidylglycerol.

6. An activated partial thromboplastin time measuring method comprising:
   a first mixing step of mixing a test plasma and a first reagent containing a phospholipid and an activator;
   a second mixing step of mixing a specimen obtained in the first mixing step and a second reagent containing a heparin neutralizer and a calcium salt; and
   a step of measuring a coagulation time of a specimen obtained in the second mixing step.

7. The activated partial thromboplastin time measuring method according to claim 6, wherein
   the heparin neutralizer is polybrene.

8. The activated partial thromboplastin time measuring method according to claim 6, wherein
   the calcium salt is calcium chloride.

9. The activated partial thromboplastin time measuring method according to claim 6, wherein
   the activator is at least one selected from the group consisting of ellagic acid, colloidal silica, and silicic anhydride.

10. The activated partial thromboplastin time measuring method according to claim 6, wherein
    the phospholipid is at least one selected from the group consisting of phosphatidylserine, phosphatidylethanolamine, phosphatidylcholine, and phosphatidylglycerol.

11. A determination method for determining the presence or absence of a blood coagulation inhibitor in a test plasma, the method comprising:
    a preparation step for preparing measurement specimens by mixing a normal plasma and a test plasma in which the blood coagulation inhibitor is suspected of being present, in at least three different ratios, a first mixing step of mixing each of the measurement specimens obtained in the preparation step and a first reagent containing a phospholipid and an activator;

a second mixing step of mixing each of specimens obtained in the first mixing step and a second reagent containing a heparin neutralizer and a calcium salt;

a step of measuring a coagulation time of each of specimens obtained in the second mixing step; and a step of determining a presence or absence of the blood coagulation inhibitor in the test plasma based on the coagulation time of each of the specimens obtained in the measuring step.

12. The method according to claim 11, wherein
the determining step is a step of obtaining a Rosner index value based on the coagulation time of each of the specimens obtained in the measuring step, and determining the presence or absence of the blood coagulation inhibitor in the test plasma based on the obtained Rosner index values.

13. The method according to claim 11, wherein
the blood coagulation inhibitor is lupus anticoagulant, acquired hemophilia, coagulation factor inhibitor, or C1 inactivator.

14. The method according to claim 11, wherein
the heparin neutralizer is polybrene.

15. The method according to claim 11, wherein
the calcium salt is calcium chloride.

16. The method according to claim 11, wherein
the activator is at least one selected from the group consisting of ellagic acid, colloidal silica, and silicic anhydride.

* * * * *